United States Patent
Karasudani (10) Patent No.: US 7,970,459 B2
(45) Date of Patent: Jun. 28, 2011

(54) SLEEPINESS LEVEL DETECTION METHOD AND APPARATUS

(75) Inventor: Ayu Karasudani, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 238 days.

(21) Appl. No.: 12/457,055

(22) Filed: May 29, 2009

(65) Prior Publication Data

US 2009/0275847 A1    Nov. 5, 2009

Related U.S. Application Data

(63) Continuation of application No. PCT/JP2006/323855, filed on Nov. 29, 2006.

(51) Int. Cl.
*A61B 5/04* (2006.01)
(52) U.S. Cl. ......... 600/509; 600/502; 600/301; 600/595
(58) Field of Classification Search .................. 600/509, 600/513, 301, 502, 595
See application file for complete search history.

(56) References Cited

U.S. PATENT DOCUMENTS

| | | |
|---|---|---|
| 2004/0243013 A1 | 12/2004 | Kawachi et al. |
| 2005/0148894 A1 | 7/2005 | Miscynski et al. |
| 2005/0234314 A1 | 10/2005 | Suzuki et al. |

FOREIGN PATENT DOCUMENTS

| | | |
|---|---|---|
| JP | 2-277435 | 11/1990 |
| JP | 8-299443 | 11/1996 |
| JP | 2002-065650 | 3/2002 |
| JP | 2004-350773 | 12/2004 |
| JP | 2006-149470 | 6/2006 |
| WO | 99/47040 | 9/1999 |

OTHER PUBLICATIONS

International Search Report of International Application No. PCT/JP2006/323855.
Extended European Search Report for corresponding European Application 06833658.5; dated Dec. 4, 2009.

*Primary Examiner* — Carl H. Layno
*Assistant Examiner* — Jon-Eric C. Morales
(74) *Attorney, Agent, or Firm* — Staas & Halsey LLP (57) ABSTRACT

A sleepiness level detection method of determining a sleepiness level of a subject, includes: detecting a heart beat signal indicating a signal of heart beats from the subject and storing the heart beat signal in a storage device; detecting amplitude peaks of the heart beat signal and detecting an interval between the amplitude peaks as a heart beat interval; and computing a spectral density corresponding to fluctuation in the heart beat interval detected and determining the sleepiness level based on a maximum frequency at which the spectral density is maximum.

15 Claims, 10 Drawing Sheets

CLUSTERING DATA

| | CLUSTER 1 | | CLUSTER 2 | | CLUSTER 3 | | CLUSTER 4 | |
|---|---|---|---|---|---|---|---|---|
| MAXIMUM FREQUENCY | MAXIMUM SPECTRAL DENSITY | MAXIMUM FREQUENCY | MAXIMUM SPECTRAL DENSITY | MAXIMUM FREQUENCY | MAXIMUM SPECTRAL DENSITY | MAXIMUM FREQUENCY | MAXIMUM SPECTRAL DENSITY | ... |
| 0.09 | 0.1 | 0.15 | 0.018 | 0.22 | 0.021 | 0.39 | 0.0062 | ... |
| 0.089 | 0.098 | 0.14 | 0.017 | 0.23 | 0.022 | 0.38 | 0.0065 | ... |
| 0.091 | 0.089 | 0.16 | 0.019 | 0.22 | 0.019 | 0.41 | 0.0006 | ... |
| 0.095 | 0.099 | 0.18 | 0.018 | 0.25 | 0.018 | 0.42 | 0.0067 | ... |
| ... | ... | ... | ... | ... | ... | ... | ... | ... |

| CLUSTER IDENTIFICATION DATA | REPRESENTATIVE FREQUENCY | REPRESENTATIVE SPECTRAL DENSITY |
|---|---|---|
| CLUSTER 1 | 0.095 | 0.097 |
| CLUSTER 2 | 0.15 | 0.017 |
| CLUSTER 3 | 0.22 | 0.021 |
| CLUSTER 4 | 0.41 | 0.006 |
| ... | ... | ... |

SLEEPINESS LEVEL DETECTION METHOD AND APPARATUS

CROSS-REFERENCE TO RELATED APPLICATION

This application is a continuation of PCT international application Ser. No. PCT/JP2006/323855 filed on Nov. 29, 2006 which designates the United States, incorporated herein by reference, the entire contents of which are incorporated herein by reference.

FIELD

The embodiments discussed herein are directed to a sleepiness level detection method and apparatus that determine the sleepiness level of a subject.

BACKGROUND

Various methods have been proposed that measure sleepiness and wakefulness level of a subject. The most reliable method to measure sleepiness and wakefulness level uses brainwaves or information of the blood flow in the brain. This method, however, imposes a great burden on the subject and therefore have not been practically used outside hospitals and research related facilities.

On the other hand, other methods use a heart beat (pulse) signal of a subject to measure sleepiness and wakefulness level of the subject without imposing a burden on the subject. For example, Japanese Laid-open Patent Publication No. 2004-350773 discloses a technology that evaluates sleepiness level of a subject depending on whether the frequency of the heart beat signal of the subject is lower than a reference value, i.e., a peak frequency of the heart beat signal in a wakeful state. Japanese Laid-open Patent Publication No. 08-299443 discloses a technology that evaluates the sleepiness level of a subject based on the strength of a low frequency portion and a high frequency portion of a heart beat signal, or based on the ratio of the low frequency portion to the high frequency portion.

The conventional technologies, however, pose a problem that the sleepiness level of the subject cannot be determined stably with the use of the heart beat signal.

In Japanese Laid-open Patent Publication No. 2004-350773, sleepiness is determined based on the band of a peak frequency of the heart beat signal. However, the heart beat signals differ among individuals and the peak frequency of the heart beat signal widely fluctuates depending on physical conditions of the subject. Thus, sleepiness level cannot be evaluated stably.

In Patent Japanese Laid-open Patent Publication No. 08-299443, the sleepiness level of the subject is evaluated based on the ratio of the low frequency portion to the high frequency portion of the heart beat signal. Because the borders between the low frequency and the high frequency differ among individuals and the fluctuation depending on the physical conditions is large, the technology cannot be used widely. Further, as to the low frequency portion and the high frequency portion, the low frequency portion is extremely large in power. Thus, if the ratio between these two portions is taken, an error in the low frequency portion greatly affects the evaluation of sleepiness level, and thus stable evaluation cannot be realized.

Thus, it has been a challenge to stably determine the sleepiness level of a subject without being affected by physical conditions of the subject or differences among individuals.

SUMMARY

According to an aspect of the invention, a sleepiness level detection method of determining a sleepiness level of a subject, includes: detecting a heart beat signal indicating a signal of heart beats from the subject and storing the heart beat signal in a storage device; detecting amplitude peaks of the heart beat signal and detecting an interval between the amplitude peaks as a heart beat interval; and computing a spectral density corresponding to fluctuation in the heart beat interval detected and determining the sleepiness level based on a maximum frequency at which the spectral density is maximum.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

DESCRIPTION OF EMBODIMENTS

Preferred embodiments of a sleepiness level detection method and a sleepiness level detection program according to the present invention are described with reference to the accompanying drawings.

[a] First Embodiment

An overview and features of a sleepiness level detection apparatus according to a first embodiment is explained. The sleepiness level detection apparatus according to the first embodiment detects a signal of heart beats from a subject (hereinafter, a heart beat signal), and detects an interval of amplitude peaks of the heart beat signal (hereinafter, a heart beat interval). The sleepiness level detection apparatus computes a spectral density corresponding to fluctuation in the heart beat interval, and determines a sleepiness level based on a frequency at which the computed spectral density is maximum.

In this manner, the sleepiness level detection apparatus according to the first embodiment computes the spectral density corresponding to the fluctuation in the heart beat interval, and determines the sleepiness level based on the frequency at which the computed spectral density is maximum. Thus, the sleepiness level detection apparatus can determine the sleepiness level of the subject stably and for general purposes without being affected by physical conditions of the subject or differences among individuals.

The heart beat interval is not a particular value dependent on the subject's physical condition or each subject, but fluctuates beat by beat being affected by that subject's cardiovascular system. The spectral density of the heart beat interval fluctuates depending on the condition of the living body. When the living body is active (awake), the sympathetic nerve is dominant, and when the living body is relaxed (for example, when getting drowsy) the parasympathetic nerve is dominant.

The sympathetic nerve increases the heart rate to increase myocardial contractility, while the parasympathetic nerve decreases the heart rate to decrease myocardial contractility. Depending on which of the nerves (whether the sympathetic nerve or the parasympathetic nerve) is dominant, the heart beat interval fluctuates differently. Thus, by analyzing the fluctuation in the heart beat interval, the change in dominance of the sympathetic nerve and the parasympathetic nerve is estimated, so that the sleepiness level can be determined stably without being affected by physical conditions of the subject or differences among individuals.

Figure 1:
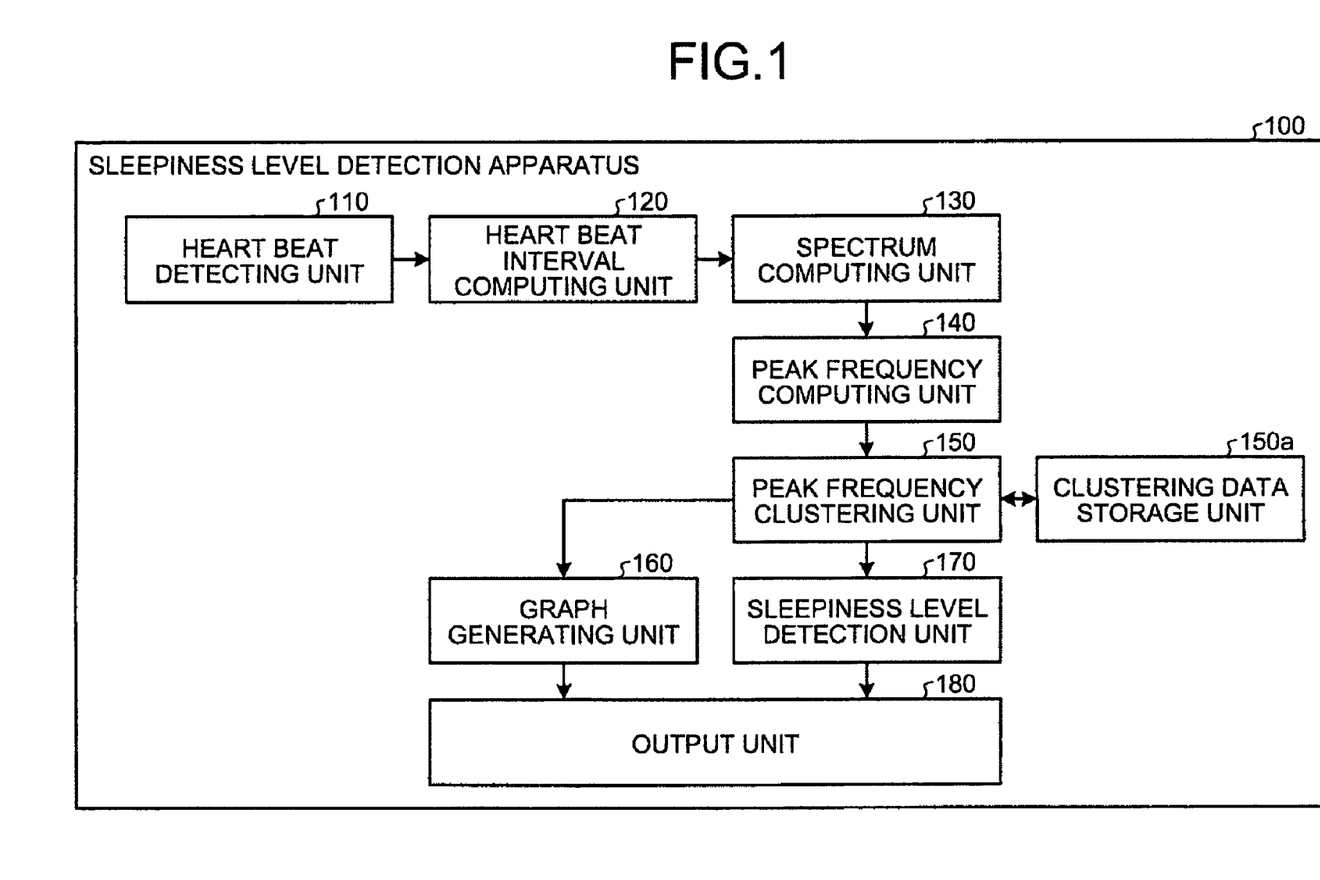
FIG. 1 is a functional block diagram of a structure of a sleepiness level detection apparatus according to a first embodiment.

A structure of the sleepiness level detection apparatus according to the first embodiment is explained. FIG. 1 is a functional block diagram of a structure of the sleepiness level detection apparatus according to the first embodiment. As illustrated in FIG. 1, a sleepiness level detection apparatus 100 includes a heart beat detecting unit 110, a heart beat interval computing unit 120, a spectrum computing unit 130, a peak frequency computing unit 140, a peak frequency clustering unit 150, a clustering data storage unit 150a, a graph generating unit 160, a sleepiness level detection unit 170, and an output unit 180.

Figure 2:
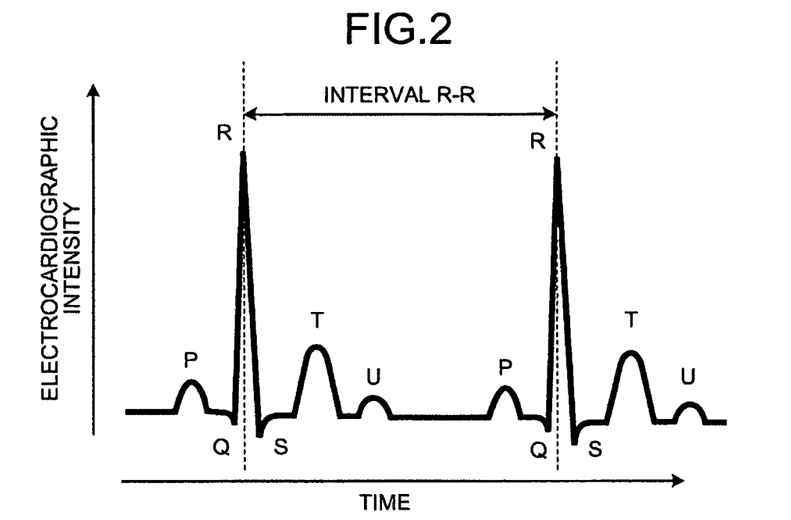
FIG. 2 is an example of a heart beat signal detected by a heart beat detecting unit.

The heart beat detecting unit 110 is a unit that detects a heart beat signal of a subject. The heart beat detecting unit 110, for example, applies voltage to electrodes in contact with the subject, and obtains the heart beat signal of the subject based on potential difference between the electrodes. FIG. 2 is an example of the heart beat signal detected by the heart beat detecting unit 110. The heart beat detecting unit 110 outputs data of the heart beat signal (hereinafter, heart beat signal data) to the heart beat interval computing unit 120.

The heart beat interval computing unit 120 is a unit that detects amplitude peaks of the heart beat signal based on the heart beat signal data, and an interval of the detected timings (hereinafter, heart beat interval). The procedure performed by the heart beat interval computing unit 120 is now described with reference to FIG. 2. As illustrated in FIG. 2, the heart beat interval computing unit 120 detects points R at which the amplitude of the heart beat signal is equal to or greater than a threshold, i.e., the amplitude peaks, and computes the interval between the detected points R (the time interval corresponding to an interval R-R). The heart beat interval computing unit 120 outputs data of the heart beat interval (hereinafter, heart beat interval data) computed to the spectrum computing unit 130. The method of detecting the amplitude peaks is not limited to the above method. For example, a method using a zero cross point where the differential coefficient of the heart beat signal changes from positive to negative, or a method detecting the peaks by performing pattern matching for amplitude waveform may be used.

Figure 3A:
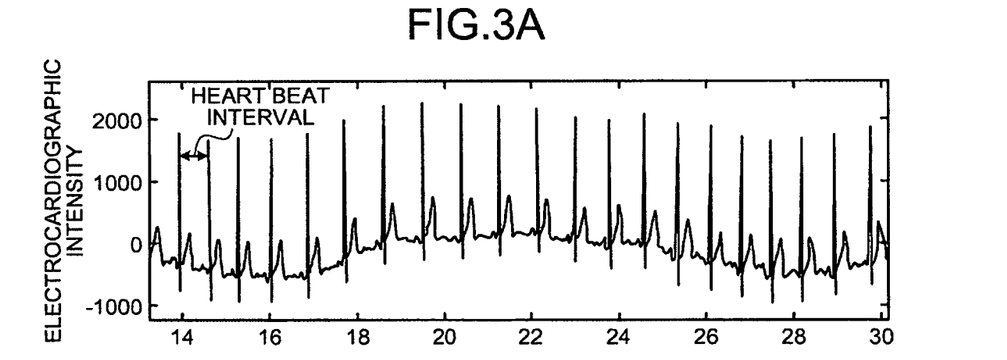
FIG. 3A is a diagram of heart beat interval fluctuation data.
Figure 3B:
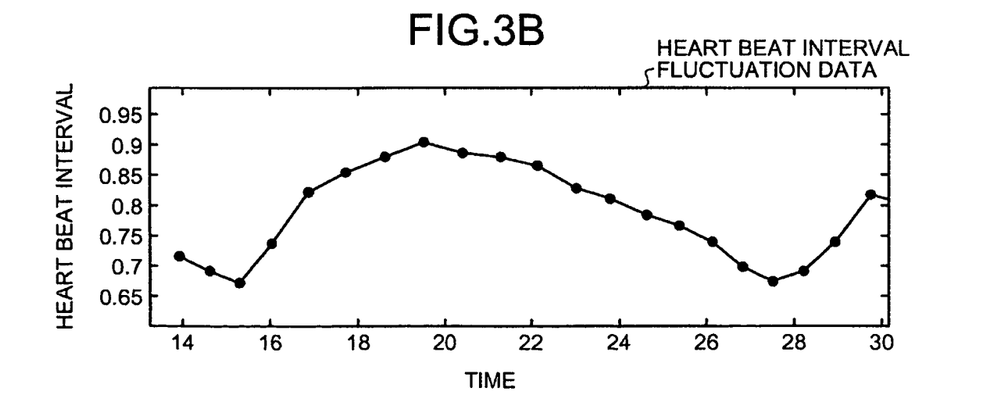
FIG. 3B is a diagram of heart beat interval fluctuation data on a heart beat interval-time plane.

The spectrum computing unit 130 is a unit that computes spectral density corresponding to fluctuation in the heart beat interval based on the heart beat interval data. A procedure performed by the spectrum computing unit 130 is now described specifically. Based on the heart beat interval data, the spectrum computing unit 130 generates data of the heart beat interval that fluctuate over time (hereinafter, heart beat fluctuation data). FIG. 3A is a diagram of heart beat interval fluctuation data and FIG. 3B is a diagram of heart beat interval fluctuation data on a heart beat interval-time plane. As illustrated in FIGS. 3A and 3B, the heart beat interval fluctuates over time.

Figure 4:
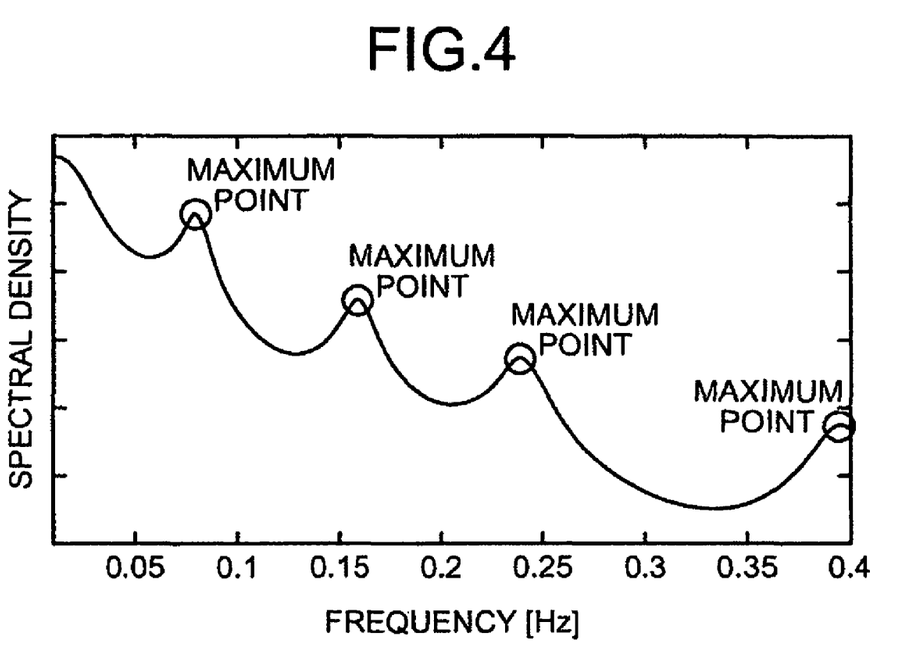
FIG. 4 is a diagram of a relationship between frequency and spectral density.

Subsequently, the spectrum computing unit 130 computes the spectral density corresponding to each frequency based on the heart beat interval fluctuation data. FIG. 4 is a diagram of a relationship between the frequency and the spectral density. As illustrated in FIG. 4, the spectral density becomes maximum at a plurality of frequencies. The spectrum computing unit 130 outputs data indicating a relationship between the computed spectral density and the frequency (hereinafter, spectral density data) to the peak frequency computing unit 140.

The spectrum computing unit 130 may use any method of computing the spectral density. The spectral density may be computed by using, for example, an autoregressive (AR) model. As disclosed in Non-Patent Document (Shunsuke Sato, Sho Kikkawa, Toru Kiryu, "Introduction to Bio-signal Processing" published by CORONA publishing Co., Ltd.) and the like, the AR model is a model that represents a state at a time point with a linear sum of previous data in time series. The AR model is characterized by obtainment of clear maximum points even with little data as compared to Fourier transform.

An AR model of order p for time series x(s) can be expressed by $$x(s) = \sum_{m=1}^{p} a(m)x(s-m) + e(s) \quad (1)$$

where a(m) is an AR coefficient being a weight relative to a past value, and e(s) is an error term (ideally, e(s) is white noise).

When p is degree of identification, $f_s$ is sampling frequency, $\epsilon_p$ is identification error, and $\hat{a}_p(k)$ is an AR coefficient of order k, spectral density $P_{AR}(f)$ can be expressed by $$P_{AR}(f) = \frac{1}{f_s} \frac{\epsilon_p}{\left|1 + \sum_{k=1}^{p} \hat{a}_p(k)e^{-2\pi jkf/f_k}\right|^2} \quad (2)$$

The spectrum computing unit 130 is able to compute the spectral density data based on Equation (2) and the heart beat interval fluctuation data.

Referring back to FIG. 1, the peak frequency computing unit 140 is a unit that computes, based on the spectral density data, a frequency at which the spectral density is maximum (hereinafter, maximum frequency) and the spectral density corresponding to the maximum frequency (hereinafter, maximum spectral density). The peak frequency computing unit 140 computes a frequency f satisfying $$\frac{dP_{AR}(f)}{df} = 0 \quad (3)$$

as the maximum frequency, and substitutes the maximum frequency into Equation (2), so as to obtain the maximum spectral density.

Figure 5A:
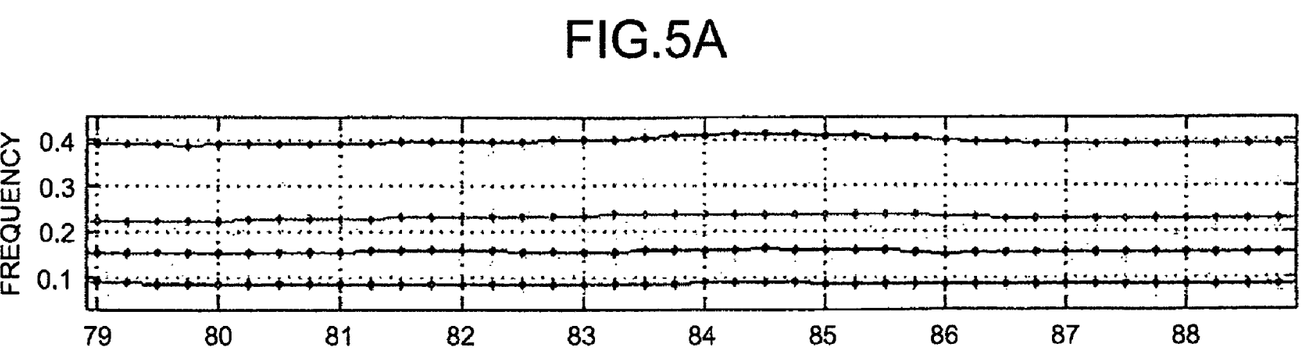
FIG. 5A is a diagram of time series of maximum frequencies.
Figure 5B:
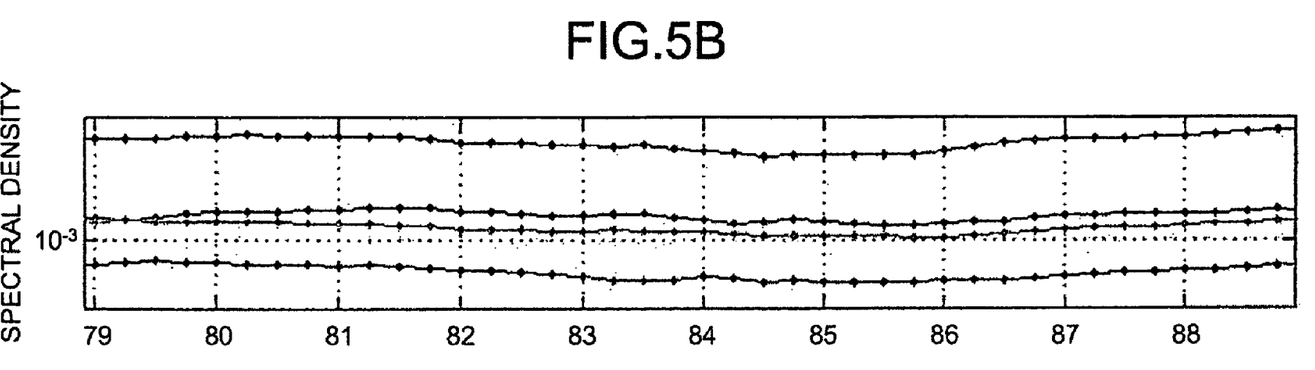
FIG. 5B is a diagram of time series of spectral densities corresponding to the maximum frequencies.

FIG. 5A is a diagram of time series of maximum frequencies and FIG. 5B is a diagram of time series of spectral densities corresponding to the maximum frequencies. For example, when the spectrum computing unit 130 computes the spectral density data every ten seconds, an interval between points in the time series direction in FIGS. 5A and 5B is 10 seconds. The peak frequency computing unit 140 outputs data of the maximum frequency and the maximum spectral density to the peak frequency clustering unit 150.

Figure 6:
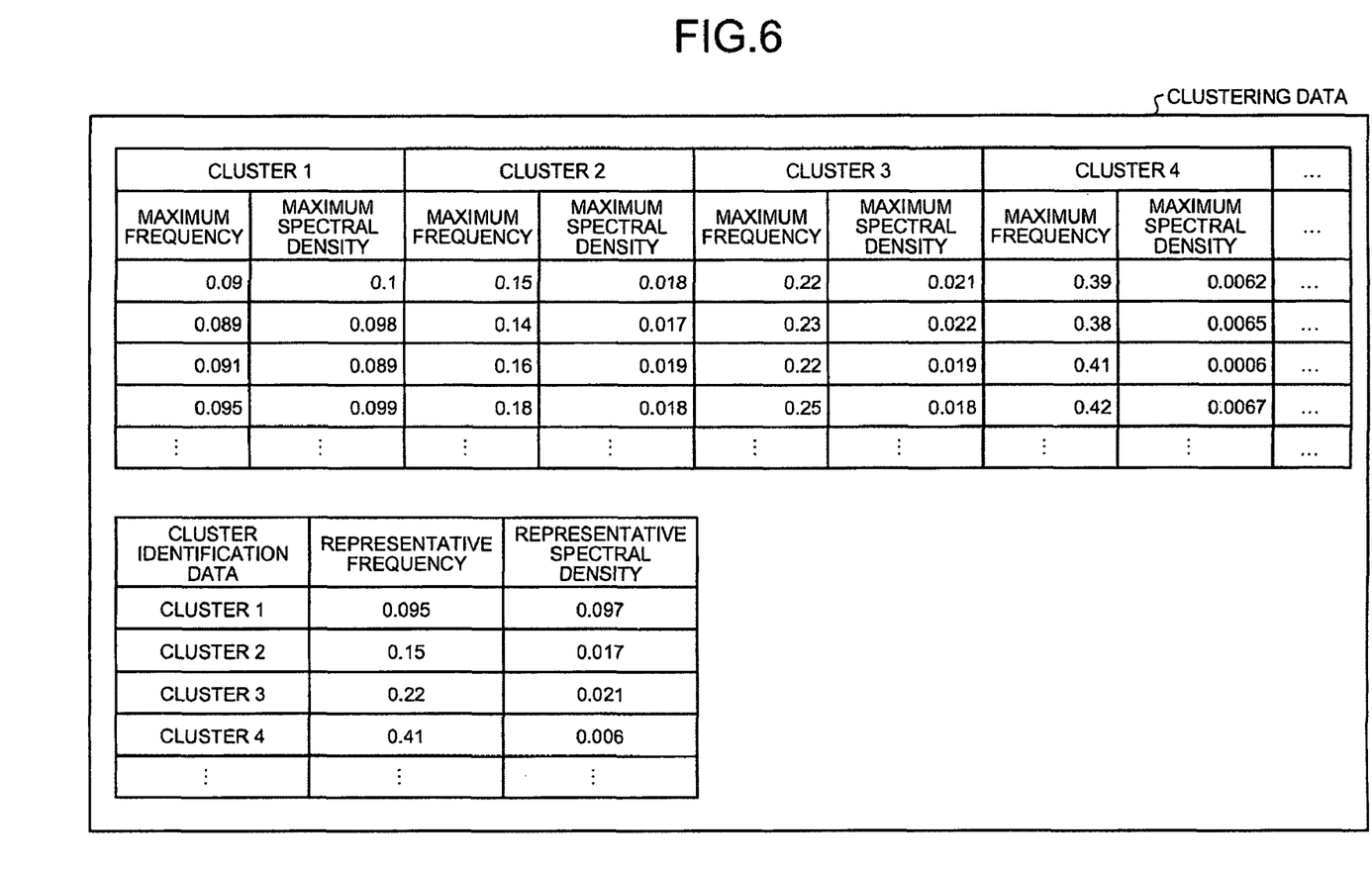
FIG. 6 is an example of a data structure of clustering data stored in a clustering data storage unit.

The peak frequency clustering unit 150 is a unit that classifies the maximum frequencies and the maximum spectral densities into a plurality of clusters, and stores the clusters into the clustering data storage unit 150a. The clustering data storage unit 150a is a unit that stores therein each cluster. FIG. 6 is an example of a data structure of clustering data stored in the clustering data storage unit 150a. As illustrated in FIG. 6, the clustering data is classified into clusters each including similar maximum frequencies (each included in a predetermined band), and the maximum frequencies are associated with the maximum spectral densities. The clustering data may be initially registered by obtaining maximum frequency and maximum spectral density data for a predetermined period of time from the start of measurement, or may be initially registered based on maximum frequency and maximum spectral density data that are unique to each individual from a database generated in advance for each individual.

A representative frequency and a representative spectral density are set for each cluster. The representative frequency is a representative value of the maximum frequencies included in each cluster, and the representative spectral density is a representative value of the maximum spectral densities included in each cluster.

The peak frequency clustering unit 150 may compute the representative frequency by computing an average of the maximum frequencies included in each cluster, and the representative spectral density by computing an average of the maximum spectral densities included in each cluster.

When the peak frequency clustering unit 150 obtains a maximum frequency from the peak frequency computing unit 140, the peak frequency clustering unit 150 compares the obtained maximum frequency with the representative frequency, and registers the maximum frequency and its corresponding maximum spectral density into a cluster whose representative frequency has a minimum difference from the maximum frequency. When an upper limit for a number of the maximum frequencies that can be registered in the cluster is exceeded, an oldest maximum frequency data is deleted from the clustering data.

The graph generating unit 160 is a unit that obtains a representative frequency and a representative spectral density (the representative frequency and the representative spectral density may correspond to any cluster; see FIG. 6) from the peak frequency clustering unit 150 every predetermined time period, generates a graph with relationship between the obtained representative frequencies and representative spectral densities plotted on a spectral density-frequency plane, and outputs the generated graph data to the output unit 180.

Figure 7:
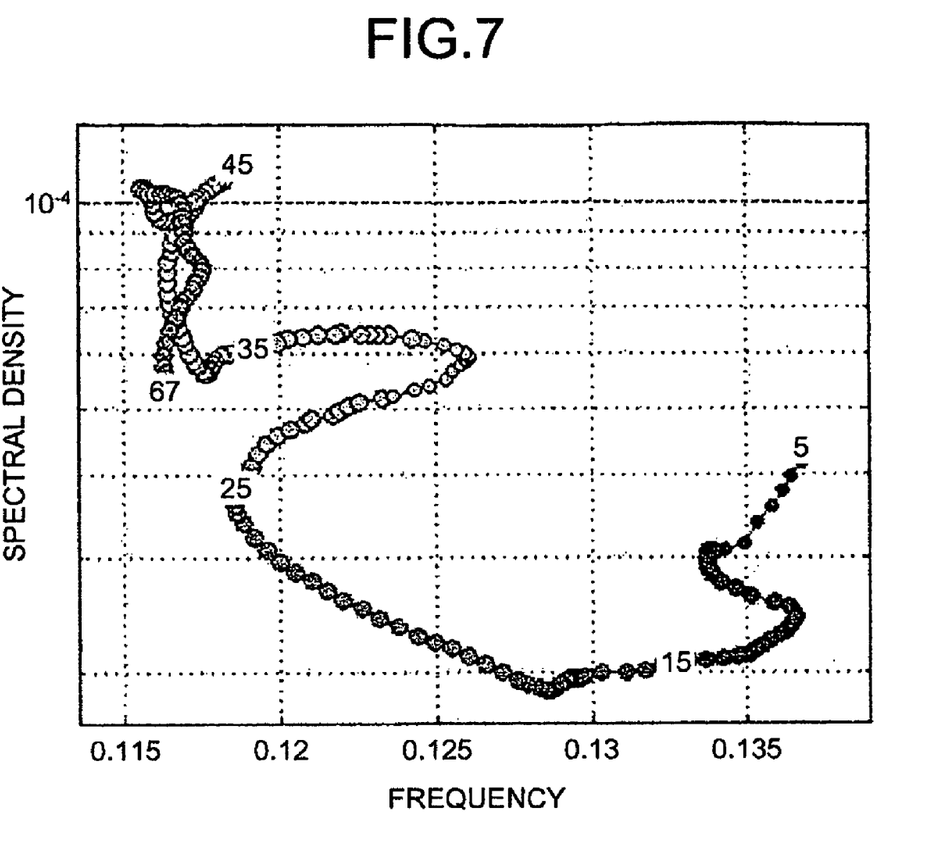
FIG. 7 is an example of a graph generated by a graph generating unit.

FIG. 7 is an example of a graph generated by the graph generating unit 160. As illustrated in FIG. 7, the relationship between the representative frequency and the representative spectral density changes every moment. A user can determine the sleepiness level of the subject by referring to the change in the relationship.

Figure 8A:
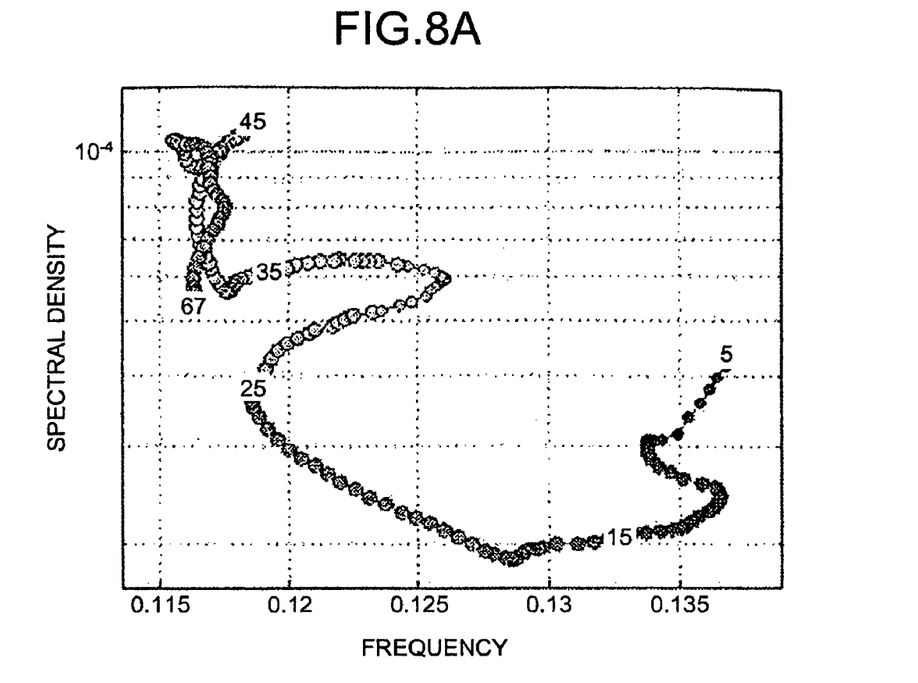
FIG. 8A is an explanatory diagram for a process of determining a sleepiness level of a subject.
Figure 8B:
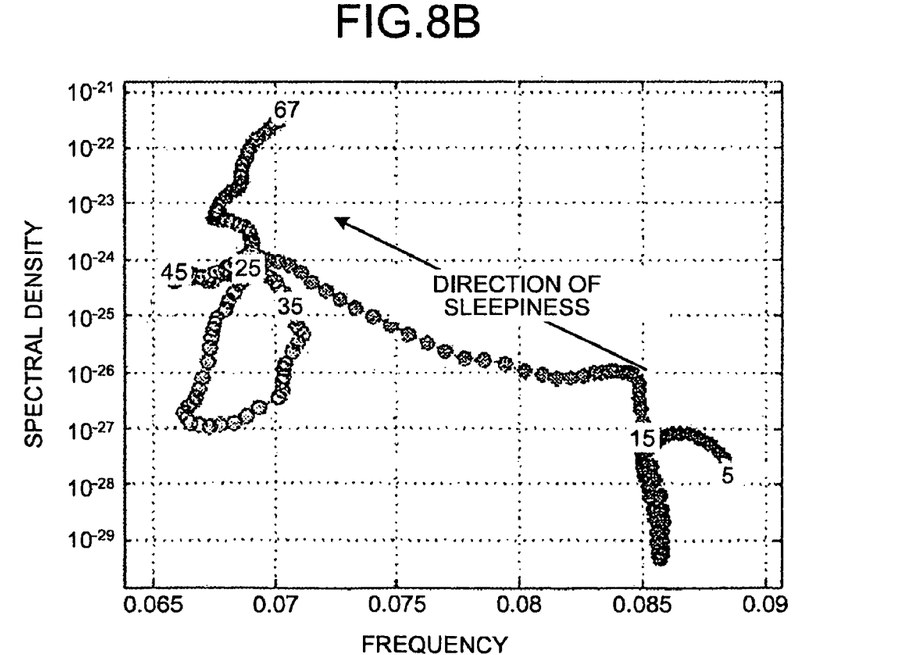
FIG. 8B is an explanatory diagram for the process of determining the sleepiness level of the subject.

FIG. 8A is an explanatory diagram for a process of determining a sleepiness level of a subject and FIG. 8B is an explanatory diagram for the process of determining the sleepiness level of the subject. As illustrated in FIGS. 8A and 8B, when the relationship between the representative frequency and the representative spectral density shifts to the upper left (the direction in which the frequency decreases and the spectral density increases), it may be determined that the subject is shifting from a wakeful state to a drowsy state.

Referring back to FIG. 1, the sleepiness level detection unit 170 is a unit that obtains the representative frequency and the representative spectral density (the representative frequency and the representative spectral density may correspond to any cluster; see FIG. 6) from the peak frequency clustering unit 150, and determines whether the subject is in the wakeful state based on fluctuation trend of the obtained representative frequency and representative spectral density.

Specifically, the sleepiness level detection unit 170 sets, as reference values, a representative frequency and a representative spectral density found at the start of determining the subject's sleepiness level, and thereafter compares the representative frequency and the representative spectral density output from the peak frequency clustering unit 150, and determines whether the subject is in the wakeful state. Hereinafter, the representative frequency and representative spectral density serving as the reference values are referred to as a reference frequency and a reference spectral density, respectively.

The sleepiness level detection unit 170 performs a first determining process of comparing the reference frequency and a representative frequency (a representative frequency newly computed by the peak frequency clustering unit), and a second determining process of comparing the reference spectral density and a representative spectral density (newly computed by the peak frequency clustering unit).

In the first determining process, when the representative frequency becomes less than the reference frequency by a value equal to or greater than a threshold value, the sleepiness level detection unit 170 determines that the subject is not in the wakeful state. Hereinafter, a determination result made in the first determining process is referred to as a first determination result.

In the second determining process, when the representative frequency density becomes greater than the reference spectral density by a value equal to or greater than a threshold value, the sleepiness level detection unit 170 determines that the subject is not in the wakeful state. Hereinafter, a determination result made in the second determining process is referred to as a second determination result.

When the subject is determined to be not in the wakeful state for both of the first determination result and the second determination result, the sleepiness level detection unit 170 finally determines that the subject is not in the wakeful state (that is, the subject is feeling drowsy), and outputs an alarm output command to the output unit 180.

The output unit 180 is a unit that outputs various information, and includes a monitor (or a display, a touch panel) and a speaker. When the output unit 180 obtains the graph data from the graph generating unit 160, the output unit 180 displays the graph on the display. When the output unit 180 obtains the alarm output command from the sleepiness level detection unit 170, the output unit 180 outputs an alarm from the speaker.

Figure 9:
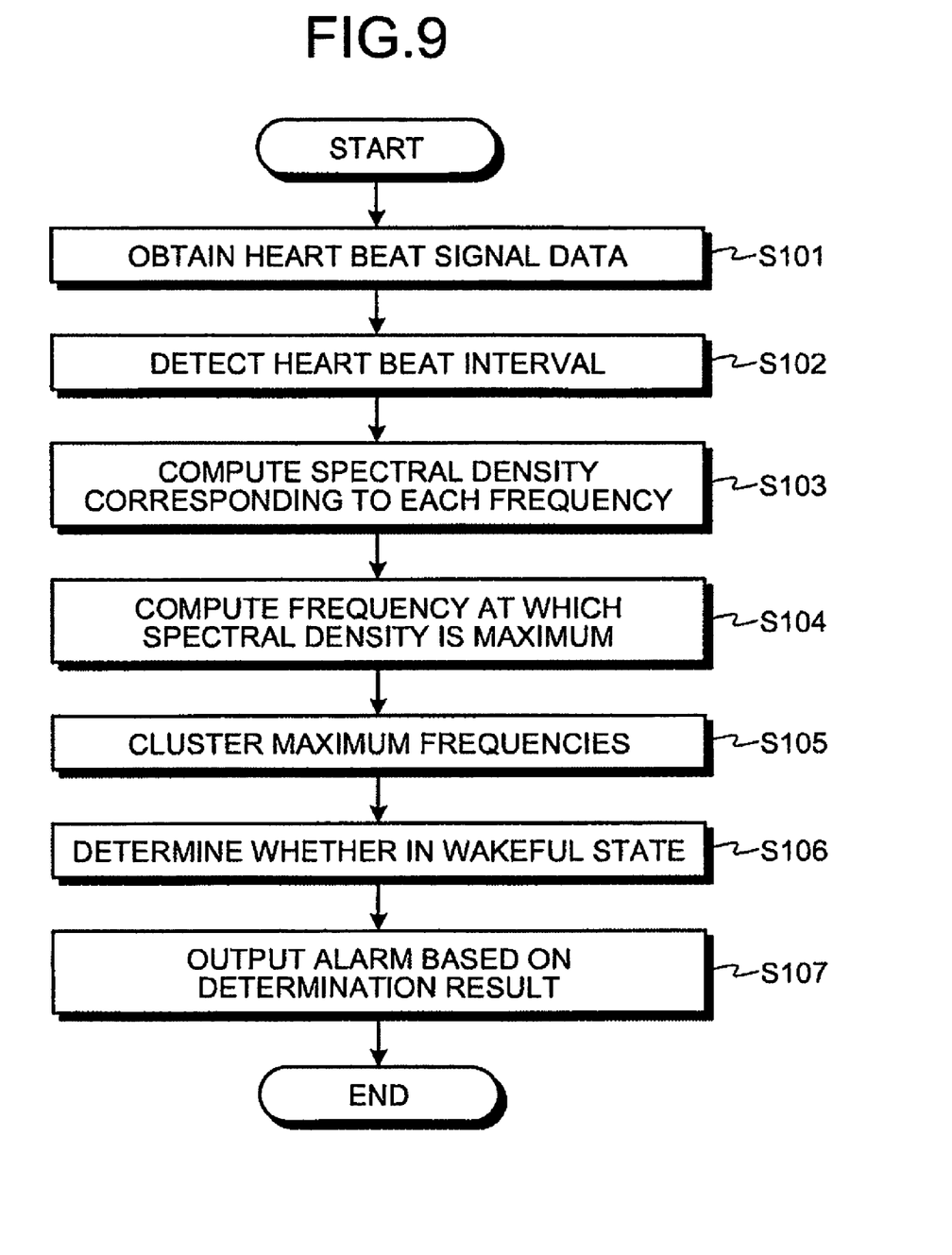
FIG. 9 is a flowchart of procedural steps performed by the sleepiness level detection apparatus according to the first embodiment.

Procedural steps performed by the sleepiness level detection apparatus 100 according to the first embodiment are explained. FIG. 9 is a flowchart of the procedural steps performed by the sleepiness level detection apparatus 100 according to the first embodiment. As illustrated in FIG. 9, in the sleepiness level detection apparatus 100, the heart beat interval computing unit 120 obtains the heart beat signal data detected by the heart beat detecting unit 110 (Step S101), and detects the heart beat interval (Step S102).

The spectrum computing unit 130 computes the spectral density corresponding to each frequency based on the heart beat interval data (Step S103). The peak frequency computing unit 140 computes the frequency at which the spectral density is maximum (Step S104).

Subsequently, the peak frequency clustering unit 150 clusters maximum frequencies and stores the clustered data in the clustering data storage unit 150a (Step S105). The sleepiness level detection unit 170 determines whether the subject is in the wakeful state based on the fluctuation trend of the representative frequency and the representative spectral density (Step S106). The output unit 180 outputs the alarm based on the determination result made by the sleepiness level detection unit 170 (Step S107).

In this manner, the sleepiness level detection unit 170 determines whether the subject is in the wakeful state based on the fluctuation trend of the representative frequency and the representative spectral density. Thus, the wakeful state of the subject can be determined stably.

As described, in the sleepiness level detection apparatus 100 according to the first embodiment, the heart beat detecting unit 110 detects the heart beat signal, the heart beat interval computing unit 120 detects the heart beat interval, and the spectrum computing unit 130 computes the spectral density corresponding to the fluctuation in the heart beat interval. The peak frequency computing unit 140 computes the maximum frequency and maximum spectral density, and the sleepiness level detection unit 170 determines whether the subject is in the wakeful state based on the fluctuation trend of the maximum frequency and the maximum spectral density. Thus, the sleepiness level detection apparatus 100 can evaluate the sleepiness level of the subject stably and for general purposes without being affected by physical conditions of the subject or differences among individuals.

In the sleepiness level detection apparatus 100 according to the first embodiment, the peak frequency clustering unit 150 classifies maximum frequencies into the plurality of clusters, and the sleepiness level detection unit 170 determines the sleepiness level of the subject using the representative values of the classified clusters. Thus, the sleepiness level of the subject can be determined more stably.

[b] Second Embodiment

An embodiment of the present invention has been described so far, but the present invention may be implemented as various different embodiments other than the first embodiment. Another embodiment included by the present invention is described as a second embodiment.

(1) Detection of Heart Beat Signal

Figure 10:
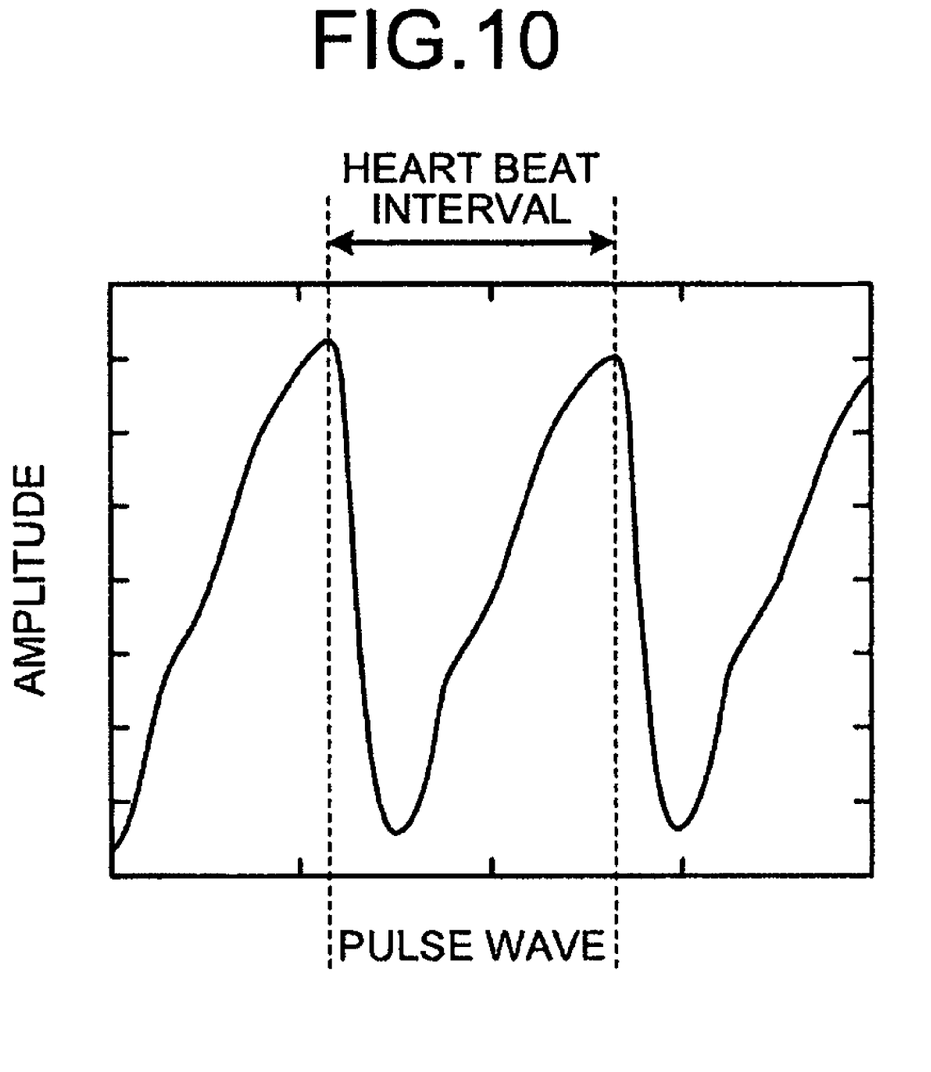
FIG. 10 is a diagram of a heart beat signal when a pulse monitor is used.

In the first embodiment, the heart beat detecting unit 110 is described as the unit that detects the heart beat signal based on the potential difference between electrodes. The present invention is not limited to this, and the heart beat detecting unit 110 may be an electrocardiograph, a pulse wave detector, a heart sound sensor, or the like, as long as it catches the subject's heart beat. FIG. 10 is a diagram of a heart beat signal when a pulse wave detector is used. To detect a heart beat interval based on such a heart beat signal, the heart beat interval computing unit 120 detects timings at which the amplitude of the heart beat signal is maximum, so as to detect a timing interval as the heart beat interval.

(2) Representative Value of Cluster

In the first embodiment, the peak frequency clustering unit 150 obtains the average value of the maximum frequencies stored in the cluster, and sets the average value as the representative frequency. The method of computing the representative value of the cluster is not limited to this.

(3) Wakeful State Determination

In the first embodiment, when the sleepiness level detection unit 170 determines that the subject is not in the wakeful state for both of the first determination result and the second determination result, the sleepiness level detection unit 170 finally determines that the subject is not in the wakeful state, and outputs the alarm output command to the output unit 180. The present invention is not limited to this. When the sleepiness level detection unit 170 determines that the subject is not in the wakeful state for either one of the first and second determination results, the sleepiness level detection unit 170 may finally determine that the subject is not in the wakeful state, and output the alarm output command to the output unit 180. The sleepiness level detection unit 170 may obtain data of number of heart beats per unit time (hereinafter, heart rate data) from the heart beat detecting unit 110, and use the heart rate data in addition, to determine the wakeful state of the subject. For example, when the sleepiness level detection unit 170 determines that the number of heart beats per unit time becomes less than a threshold based on the heart rate data and that the subject is not in the wakeful state for the first determination result and the second determination result, the sleepiness level detection unit 170 may finally determine that the subject is not in the wakeful state. When the number of heart beats per unit time is determined to exceed the threshold based on the heart rate data, the sleepiness level detection unit 170 may finally determine that the subject is in the wakeful state. As such, the sleepiness level detection unit 170 can determine the wakeful state of the subject more accurately by using the heart rate data in addition.

(4) Generation of Graph

In the first embodiment, the graph generating unit 160 obtains the representative frequency and the representative spectral density every predetermined period of time, and generates the graph in which the relationship between the obtained representative frequencies and representative spectral densities is plotted. The present invention is not limited to this. That is, the number of heart beats, the representative frequency, and the representative spectral density may be obtained every predetermined period of time to generate a graph in which the relationship between the obtained number of heart beats and representative frequency or between the number of heart beats and representative spectral density is plotted, and output the graph to the output unit 180. The graph generating unit 160 may change the color of the plotted lines over time. The graph generating unit 160 may change the size of the marker or the thickness of the lines according to the number of data stored in the cluster.

(5) Cooperation with Car Navigation

The sleepiness level detection apparatus 100 according to the first embodiment may be cooperated with a car navigation mounted on an automobile or the like. For example, the position of the automobile and road conditions that can be obtained from the car navigation, and the representative frequency and the representative spectral density may be stored in correspondence with each other. As a result, an environment the automobile is in where the subject tends to (or tends not to) fall in the wakeful state can be easily analyzed. The graph generated by the graph generating unit 160 may be output to the monitor of the car navigation. When the car navigation includes two displays available for the driver seat side and the front passenger seat side, the graph generated by the graph generating unit 160 may be displayed only at the front passenger seat side display. By displaying the graph only at the display at the front passenger seat side, the driver can feel less discomfort, and the passenger on the front passenger seat can feel secure.

(6) Process Performed by Peak Frequency Computing Unit

The peak frequency computing unit 140 according to the first embodiment computes the maximum frequency at which the spectral density is maximum and the spectral density corresponding to the maximum frequency (maximum spectral density) based on the spectral density data. The present invention is not limited to this. A minimum frequency at which the spectral density is minimum and a spectral density corresponding to the minimum frequency (minimum spectral density) may be computed based on the spectral density data, and the peak frequency clustering unit 150, the graph generating unit 160, and the sleepiness level detection unit 170 may perform the various processes (such as generation of a graph, and determination of the sleepiness level) using the values of the minimum frequency and the minimum spectral density instead of the maximum frequency and the maximum spectral density.

(7) System Configuration

As to the processes described in the present embodiment, all or part of the processes described as being performed automatically can be performed manually. Alternatively, as to the processes described as being performed manually, all or part of the processes can be performed automatically by know methods. In addition, processing procedures, controlling procedures, specific names, information including various data and parameters described in the description and the accompanying drawings can be changed in any way, unless otherwise specified.

Each structural element of the sleepiness level detection apparatus 100 illustrated has been described functionally/conceptually, and is not necessarily physically structured as illustrated in the drawings. Thus, specific forms of distribution and integration of each device are not limited to those illustrated in the drawings, and all or part of each device may be distributed/integrated functionally or physically by any unit according to various loads and use conditions. Further, all or any part of processes and functions performed by each device may be implemented by a central processing unit (CPU) or a computer program interpretable and executable by the CPU, or implemented by hardware using wired logic.

Figure 11:
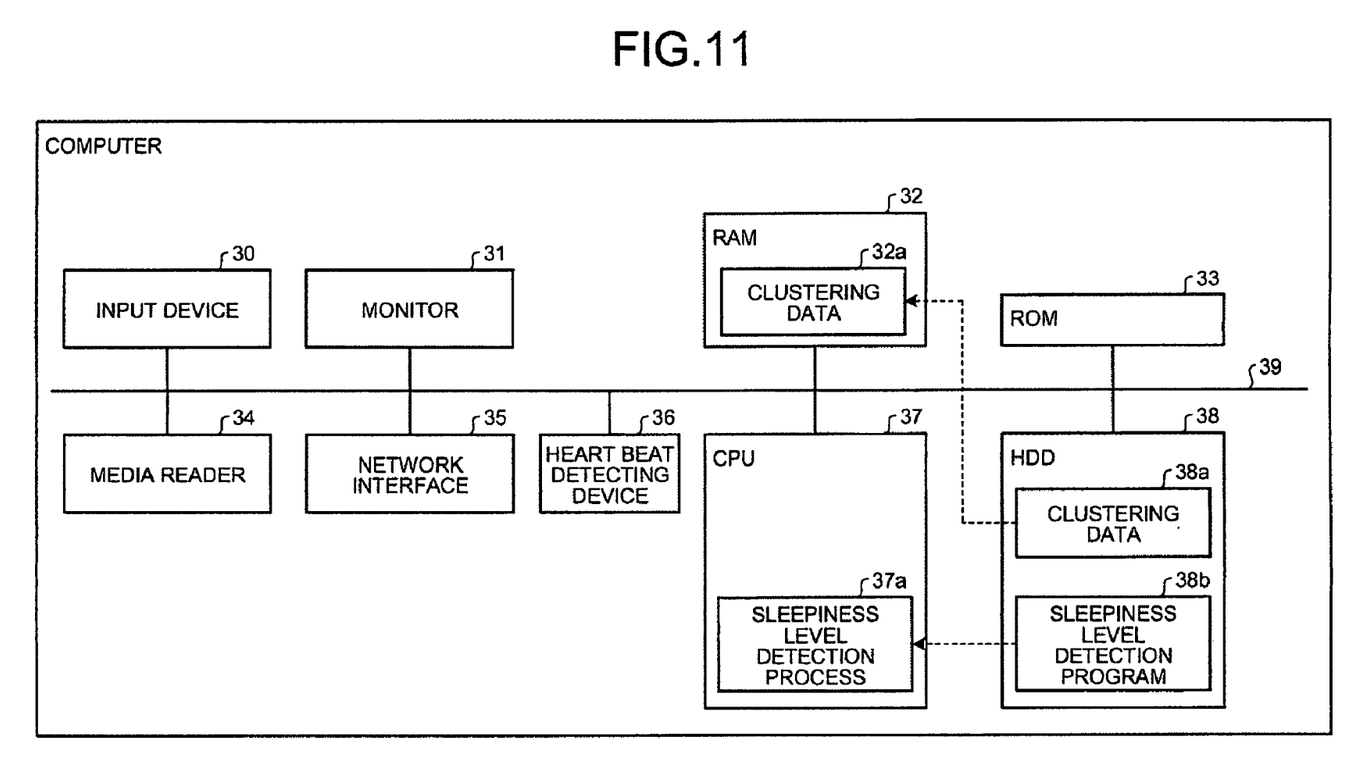
FIG. 11 is a diagram of a hardware structure of a computer that constitutes the sleepiness level detection apparatus illustrated in FIG. 1.

FIG. 11 is a diagram of a hardware structure of a computer that constitutes the sleepiness level detection apparatus 100 illustrated in FIG. 1. The computer includes an input device 30 that receives data input from a user, a monitor 31, a random access memory (RAM) 32, a read only memory (ROM) 33, a media reader 34 that reads a computer program from a recording medium storing therein various computer programs, a network interface 35 that communicates data with another computer via a network, a heart beat detecting device 36 (corresponding to the heart beat detecting unit 110) that detects the heart beats of the subject, a CPU 37, and a hard disk drive (HDD) 38, that are connected to each other via a bus 39.

The HDD 38 stores therein a sleepiness level detection program 38b that performs functions similar to those of the sleepiness level detection apparatus 100. The CPU 37 reads the sleepiness level detection program 38b from the HDD 38 and executes the program, and accordingly a sleepiness level detection process 37a is activated that implements the functions of the functional parts of the sleepiness level detection apparatus 100. The sleepiness level detection process 37a corresponds to the heart beat interval computing unit 120, the spectrum computing unit 130, the peak frequency computing unit 140, the peak frequency clustering unit 150, the graph generating unit 160, and the sleepiness level detection unit 170 illustrated in FIG. 1.

The HDD 38 stores therein clustering data 38a that corresponds to the data stored in the clustering data storage unit 150a of the sleepiness level detection apparatus 100. The clustering data 38a corresponds to the clustering data illustrated in FIG. 6. The CPU 37 stores the clustering data 38a in the HDD 38. Further, the CPU 37 reads the clustering data 38a from the HDD 38, stores the data in the RAM 32, and performs a sleepiness level detection process using clustering data 32a stored in the RAM 32.

The sleepiness level detection program 38b is not necessarily stored initially in the HDD 38. For example, the sleepiness level detection program 38b may be stored in: a "portable physical medium" such as a flexible disk (FD), a compact disk read only memory (CD-ROM), a digital versatile disk (DVD disk), a magneto optic disk, or an integrated circuit (IC) card inserted in the computer; a "fixed physical medium" such as a HDD mounted inside or outside the computer; or, "another computer (or server)" connected to the computer via a public line, the Internet, a local area network (LAN), a wide area network (WAN), or the like. The computer may read the sleepiness level detection program 38b from such a medium and executes the program.

According to an embodiment of the present invention, a heart beat signal indicating a signal of heart beats is detected from a subject, and stored in a storage device. Amplitude peaks of the heart beat signal are detected, and the interval between the amplitude peaks is detected as a heart beat interval. A spectral density corresponding to fluctuation in the detected heart beat interval is computed, and a sleepiness level is determined based on a frequency at which the spectral density is maximum. Thus, the sleepiness level of the subject can be stably determined without being affected by physical conditions of the subject or differences among individuals.

According to another embodiment of the present invention, the frequencies at which the spectral density is maximum is classified into a plurality of clusters, a representative value of a plurality of frequencies included in each of the clusters is determined, and the sleepiness level is determined based on a change in the representative value and on the spectral density corresponding to the frequency of the representative value. Thus, the sleepiness level of the subject can be determined more stably.

According to yet another embodiment of the present invention, when the maximum frequency decreases and/or magnitude of the spectral density corresponding to the maximum frequency increases, it is determined that the sleepiness level has decreased. Thus, the sleepiness level of the subject can be determined more stably.

According to still another embodiment of the present invention, a graph is generated that indicates the fluctuation in the frequency at which the spectral density is maximum, and the generated graph is output. Thus, a user referring to the graph can easily determine a wakeful state of the subject.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiment(s) of the present inventions have been described in detail, it should be understood that the various changes, substitutions, and alterations could be made hereto without departing from the spirit and scope of the invention.

What is claimed is:

1. A sleepiness level detection method of determining a sleepiness level of a subject, comprising:
    detecting a heart beat signal indicating a signal of heart beats from the subject and storing the heart beat signal in a storage device;
    detecting amplitude peaks of the heart beat signal and detecting an interval between the amplitude peaks as a heart beat interval; and
    computing a spectral density corresponding to fluctuation in the heart beat interval detected and determining the sleepiness level based on a maximum frequency at which the spectral density is maximum.

2. The sleepiness level detection method according to claim 1, wherein the determining includes:
    classifying maximum frequencies at which the spectral density is maximum into a plurality of clusters;
    determining a representative value of the maximum frequencies included in each cluster; and
    determining the sleepiness level based on change in the representative value and the spectral density corresponding to a frequency of the representative value.

3. The sleepiness level detection method according to claim 2, wherein the determining of the sleepiness level includes determining that the sleepiness level has decreased if the maximum frequency decreases and/or a magnitude of the spectral density corresponding to the maximum frequency increases.

4. The sleepiness level detection method according to claim 3, wherein the determining of the representative value includes generating a histogram of the maximum frequencies stored in each cluster and determining the representative value based on the histogram.

5. The sleepiness level detection method according to claim 1, further comprising generating a graph indicating fluctuation in the maximum frequency, and outputting the graph generated.

6. A non-transitory computer readable storage medium containing instructions that, when executed by a computer, cause the computer to perform, for determining a sleepiness level of a subject:
    detecting a heart beat signal indicating a signal of heart beats from the subject and storing the heart beat signal in a storage device;
    detecting amplitude peaks of the heart beat signal and detecting an interval between the amplitude peaks as a heart beat interval; and
    computing a spectral density corresponding to fluctuation in the heart beat interval detected and determining the sleepiness level based on a maximum frequency at which the spectral density is maximum.

7. The non-transitory computer readable storage medium according to claim 6, wherein the determining includes:
    classifying maximum frequencies at which the spectral density is maximum into a plurality of clusters;
    determining a representative value of the maximum frequencies included in each cluster; and
    determining the sleepiness level based on change in the representative value and the spectral density corresponding to a frequency of the representative value.

8. The non-transitory computer readable storage medium according to claim 7, wherein the determining of the sleepiness level includes determining that the sleepiness level has decreased if the maximum frequency decreases and/or a magnitude of the spectral density corresponding to the maximum frequency increases.

9. The non-transitory computer readable storage medium according to claim 8, wherein the determining of the representative value includes generating a histogram of the maximum frequencies stored in each cluster and determining the representative value based on the histogram.

10. The non-transitory computer readable storage medium according to claim 6, wherein the computer is caused to further perform generating a graph indicating fluctuation in the maximum frequency, and outputting the graph generated.

11. A sleepiness level detection apparatus that determines a sleepiness level of a subject, comprising:
    a heart beat signal detecting unit that detects a heart beat signal indicating a signal of heart beats from the subject;
    a heart beat interval detecting unit that detects amplitude peaks of the heart beat signal, and an interval of the amplitude peaks as a heart beat interval; and
    a sleepiness level detection unit that computes a spectral density corresponding to fluctuation in the heart beat interval detected by the heart beat interval detecting unit, and determines the sleepiness level based on a maximum frequency at which the spectral density is maximum.

12. The sleepiness level detection apparatus according to claim 11, wherein the sleepiness level detection unit includes:
    a classifying unit that classifies maximum frequencies at which the spectral density is maximum into a plurality of clusters;
    a representative value determining unit that determines a representative value of the maximum frequencies included in each cluster; and
    a determining unit that determines the sleepiness level based on change in the representative value and the spectral density corresponding to a frequency of the representative value.

13. The sleepiness level detection apparatus according to claim 12, wherein the determining unit determines that the sleepiness level has decreased if the maximum frequency decreases and/or a magnitude of the spectral density corresponding to the maximum frequency increases.

14. The sleepiness level detection apparatus according to claim 13, wherein the representative value determining unit generates a histogram of the maximum frequencies stored in each cluster, and determines the representative value based on the histogram.

15. The sleepiness level detection apparatus according to claim 11, further comprising a graph output unit that generates a graph indicating fluctuation in the maximum frequency, and outputs the graph generated.

* * * * *